United States Patent
Namati et al.

(10) Patent No.: US 9,237,851 B2
(45) Date of Patent: Jan. 19, 2016

(54) IMAGING SYSTEM PRODUCING MULTIPLE REGISTERED IMAGES OF A BODY LUMEN

(75) Inventors: Eman Namati, Arlington, MA (US); James W. Moriarty, Jr., Georgetown, MA (US); Michael Madden, Princeton, MA (US)

(73) Assignee: NINEPOINT MEDICAL, INC., Cambridge, MA (US)

(*) Notice: Subject to any disclaimer, the term of this patent is extended or adjusted under 35 U.S.C. 154(b) by 213 days.

(21) Appl. No.: 13/365,621

(22) Filed: Feb. 3, 2012

(65) Prior Publication Data

US 2013/0204126 A1    Aug. 8, 2013

(51) Int. Cl.
| | |
|---|---|
| A61B 6/00 | (2006.01) |
| A61B 5/00 | (2006.01) |
| A61B 8/12 | (2006.01) |
| A61B 1/00 | (2006.01) |
| A61B 19/00 | (2006.01) |

(52) U.S. Cl.
CPC ............. *A61B 5/0066* (2013.01); *A61B 5/0035* (2013.01); *A61B 5/0084* (2013.01); *A61B 8/12* (2013.01); *A61B 1/0005* (2013.01); *A61B 2019/5289* (2013.01); *A61B 2019/5425* (2013.01); *A61B 2019/5437* (2013.01)

(58) Field of Classification Search
CPC combination set(s) only.
See application file for complete search history.

(56) References Cited

U.S. PATENT DOCUMENTS

| | | | |
|---|---|---|---|
| 6,498,948 B1* | 12/2002 | Ozawa et al. | 600/476 |
| 7,733,497 B2 | 6/2010 | Yun et al. | |
| 7,742,797 B2* | 6/2010 | Redel | 600/407 |
| 2004/0210106 A1* | 10/2004 | Banju | 600/102 |
| 2007/0038062 A1* | 2/2007 | Redel | 600/407 |
| 2007/0066890 A1 | 3/2007 | Maschke | |
| 2007/0135887 A1 | 6/2007 | Maschke | |
| 2007/0232861 A1* | 10/2007 | Kohno et al. | 600/160 |
| 2008/0021275 A1 | 1/2008 | Tearney et al. | |
| 2009/0076491 A1* | 3/2009 | Roschak et al. | 606/21 |
| 2010/0210937 A1 | 8/2010 | Tearney et al. | |

FOREIGN PATENT DOCUMENTS

| | | |
|---|---|---|
| WO | 2008086613 A1 | 7/2008 |
| WO | 2009137659 A1 | 11/2009 |

OTHER PUBLICATIONS

PCT/US2013/023801—Notification of Transmittal of the International Search Report and the Written Opinion of the International Searching Authority; International Search Report, Written Opinion of the International Searching Authority.

* cited by examiner

*Primary Examiner* — Katherine Fernandez
*Assistant Examiner* — Farshad Negarestan
(74) *Attorney, Agent, or Firm* — Sorell, Lenna & Schmidt, LLP (57) ABSTRACT

Systems, devices and methods for producing registered images of a body lumen are provided. The system includes a first imaging device having an imager positioned at a distal end thereof, said first imaging device configured to produce a first image of a body cavity; and an imaging system, including a second imaging device having an imager positioned at a distal end thereof and configured to be positioned approximate to said imager of said first imaging device within said body cavity and configured to produce a second image; an elongated member configured to contain said second imaging device; and at least one marker configured to produce registration information in the first image and the second image.

26 Claims, 11 Drawing Sheets

IMAGING SYSTEM PRODUCING MULTIPLE REGISTERED IMAGES OF A BODY LUMEN

TECHNICAL FIELD

The present disclosure generally relates to medical devices, systems and methods for imaging in biomedical and other medical and non-medical applications where multiple images are created.

BACKGROUND

Various forms of imaging systems are used in healthcare to produce images of a patient. In some instances multiple images may be produced of the same or similar anatomical locations, such as by one or more imaging devices. There is a need for an imaging system that correlates or otherwise registers multiple patient images. This disclosure describes an improvement over these prior art technologies.

SUMMARY

Accordingly, an imaging system is provided that includes a first imaging device having an imager positioned at a distal end thereof, said first imaging device configured to produce a first image of a body cavity; and an imaging system, comprising a second imaging device having an imager positioned at a distal end thereof and configured to be positioned approximate to said imager of said first imaging device within said body cavity and configured to produce a second image; an elongated member configured to contain said second imaging device; and at least one marker configured to produce registration information in the first image and the second image.

In one embodiment, an imaging system includes an imaging device for producing at least two images within a cavity of a patient, each imaging device having a distal imaging end; at least one marker positioned relative to the imaging end and configured to produce registration data in the images produced by the imaging device, said marker positioned such that the registration data will be produced in the images independent of translation and rotation of the imaging device; and a processor in communication with the imaging device configured to receive said images and register the images based on the registration data.

In one embodiment, a method for registering images in a system having a first imaging device configured to produce a first image and an imaging system including a second imaging device positioned within an elongated member, said second imaging device rotatable and configured to produce a second image, including inserting said first imaging device into a cavity of a patient; inserting said imaging system positioned with said elongated member into the cavity of the patient; said elongated member having at least one marker visible to both the first and second imaging devices; producing by said first imaging device a first image containing an image of said marker; producing by said second imaging device a second image containing an image of said marker; and registering said first image and said second image based on the image of the marker in the first and second images.

In one embodiment, an imaging system includes a first imaging device constructed and arranged to produce a first image of tubular tissue within the body cavity, said first image including first registration data; and a second imaging device constructed and arranged to produce a second image of the tubular tissue within the body cavity, said second image including second registration data, wherein the system is constructed and arranged to register the first image to the second image.

BRIEF DESCRIPTION OF THE DRAWINGS

The present disclosure will become more readily apparent from the specific description accompanied by the following drawings, in which.

Like reference numerals indicate similar parts throughout the figures.

DETAILED DESCRIPTION

The present disclosure may be understood more readily by reference to the following detailed description of the disclosure taken in connection with the accompanying drawing figures, which form a part of this disclosure. It is to be understood that this disclosure is not limited to the specific devices, methods, conditions or parameters described and/or shown herein, and that the terminology used herein is for the purpose of describing particular embodiments by way of example only and is not intended to be limiting of the claimed disclosure.

Also, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure. For example, the references "superior" and "inferior" are relative and used only in the context to the other, and are not necessarily "upper" and "lower".

Reference will now be made in detail to the exemplary embodiments of the present disclosure, which are illustrated in the accompanying figures.

Figure 1:
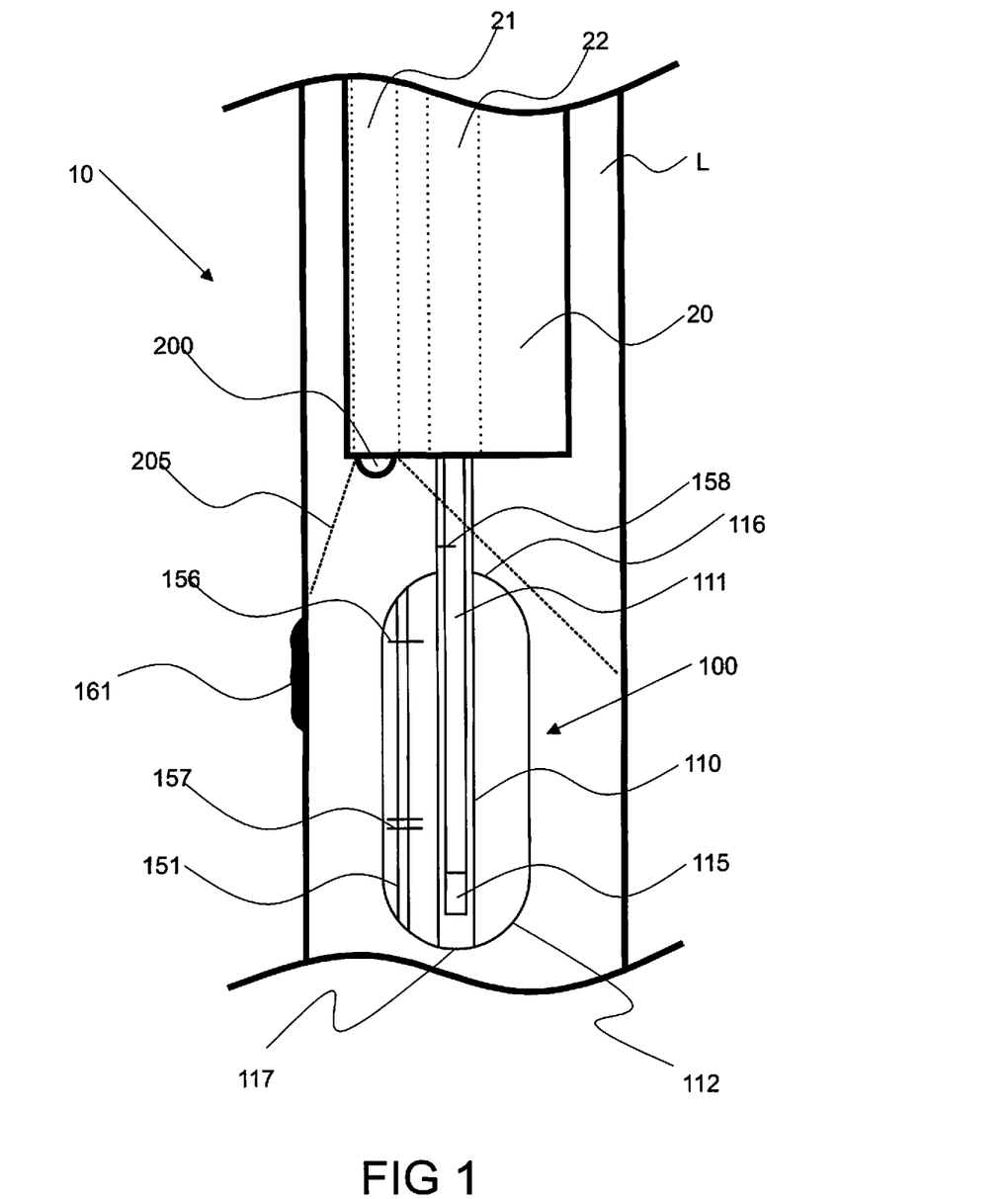
FIG. 1 is a side view of a distal portion of an imaging system for producing multiple registered images of a body lumen in accordance with the principles of the present disclosure.

FIG. 1 illustrates a side view of a distal portion of an imaging system for producing multiple registered images of a body lumen. System 10 includes a first imaging device 200, e.g. a camera, which is integral to a body introduction device, endoscope 20. Endoscope 20 has been positioned into a body lumen L, such as the esophagus of a patient. First imaging device 200 typically comprises a visible light camera, with field of view 205. Camera 200 may comprise an elongate shaft that is slidingly received by endoscope 20, such as through a working channel 21. Alternatively, camera 200 may be fixedly attached to a distal portion of endoscope 20, with wires or other conduits traveling proximally to one or more image display devices, not shown but typical to endoscopic visualization systems.

System 10 further includes a second imaging device 100, e.g. an optical coherence tomography (OCT) device. OCT device 100 includes an elongate shaft 110, which has been slidingly passed through working channel 22 of endoscope 20. OCT device includes balloon 112, including proximal end 116 and distal end 117 and shown in a partially inflated state. Although the present disclosure is described with reference to a balloon about the imaging device, other containment configurations are possible. For example, a shaft having a closed end can be used instead of the balloon to contain and protect the imaging device. Balloon 112 and shaft 110 are advanced through channel 22 while balloon 112 is in a compressed state, such as prior to expansion and/or through the application of a vacuum. In configurations where the shaft is used, the shaft is configured to be advanced through channel 22. Shaft 110 slidingly receives an inner member 111, typically a fiber optic cable configured to transmit light energy. On the distal portion of inner member 111 is mounted an imaging assembly 115 comprising one or more components commonly found in rotating and/or translating imaging devices. These components can include mirrors, lenses, filters, prisms and combinations thereof; other components are contemplated. In typical operation, balloon 112 is inflated to contact the tissue of lumen L prior to and during creation of images by OCT device 100.

Camera 200 with field of view 205 is positioned to provide end view images of lumen L, typically including a view of at least the proximal end of balloon 112. Alternatively, camera 200 may comprise a stereoscopic camera such as that described in reference to FIG. 5 herebelow. OCT Device 100 is constructed and arranged to produce at least a two-dimensional cross sectional image of lumen L at the axial location of imaging assembly 115. In some embodiments, OCT device 100 is constructed and arranged to produce a three-dimensional reconstructed image of lumen L, such as by both rotating and translating imaging assembly 115 (i.e. by rotating and translating inner member 111 via a rotating and translating assembly, not shown, but typically located at or about a proximal end of endoscope 20) As an alternate configuration, imaging assembly 115 can be rotated using a rotating motor positioned at the distal end of inner member 111, and translated using proximal advancement and pullback. Other translation and rotation means are contemplated. Multiple cross-sectional "slices" can be combined into a three-dimensional image. The slices may comprises helical slices, such as when inner member 111 and imaging assembly 115 translate at a constant velocity, or they may be planar slices such as when inner member 111 and imaging assembly 115 translate after, but not during, each 360° revolution of inner member 111 and imaging assembly 115 (e.g. in a step-wise fashion), or other combinations thereof.

System 10 further includes one or more registration markers (e.g. registration markers 151 and 156-158) positioned to be viewed by camera 200 and/or OCT device 100, which are included in images produced by camera 200 and/or the two-dimensional or three-dimensional images produce by OCT device 100. In a typical embodiment, a first image is produced by first imaging device 100, and a second image is produced by either first imaging device 100 or second imaging device 200. The first image and second image each include registration data (e.g. images of the one or more registration markers). The first image and the second image can be registered based on this registration data. The registering can be performed automatically, such as by one or more algorithms included in system 10 and/or manually, such as by an operator of system 10. Registering of the first image to the second image can include radially registering by rotating one or both images to radially orient the images to each other or to a common frame of reference, longitudinally registering the images to each other or a common frame of reference, scaling the images such as enlarging or shrinking one or both images to similarly scale the images (e.g. similar scaling of image dimensions to actual anatomical dimensions), axially or radially correlating the images (e.g. provide information related to radial displacement, longitudinal displacement and/or scaling differences), and other combinations thereof.

The registration markers may be one or more integral components to the system, such as registration markers 151, 156, 157 and 158, or the registration marker may comprise an anatomical landmark, such as a vessel or tissue mark 161. Alternatively, tissue mark 161 may be created by system 10. Mark 161 can include dyed tissue, tissue modified to reflect light, tissue modified to absorb light, tissue modified to scatter light, tissue modified by energy such as tissue scarred by laser energy delivered by OCT device 100, tissue proximate biopsied or other removed tissue, tissue mark in tissue, an implant such as a removable tissue implant such as a removable implanted filament placed through endoscope 20, and various combinations thereof. In some embodiments, system 10 can include a separate tissue marking device, such as described in reference to FIGS. 6, 7A and 7B herebelow. Other tissue marking devices are contemplated.

Figure 1A:
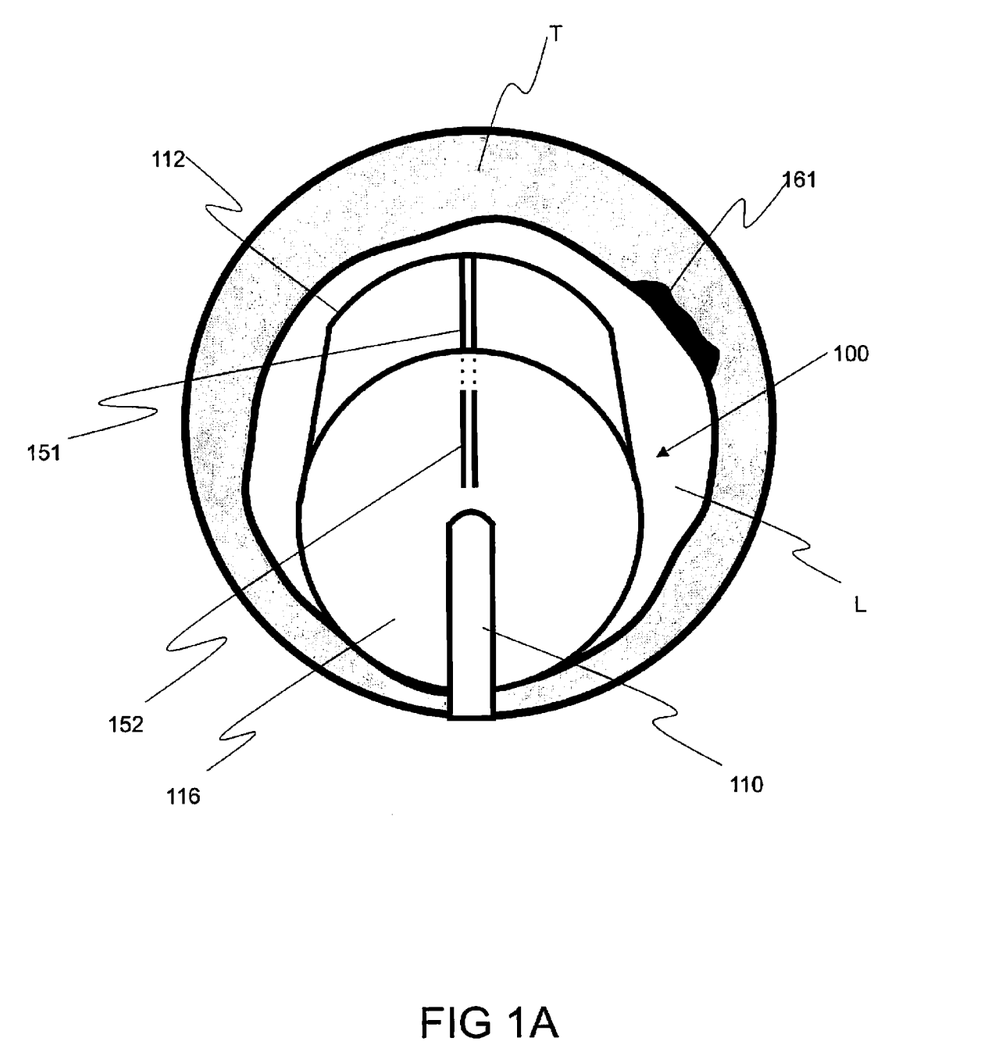
FIG. 1A is a representative drawing of an image produced by an imaging device of the imaging system of FIG. 1.

OCT Device 100 includes registration marker 151, positioned on an inner or outer surface of balloon 112, and/or within the wall thickness of balloon 112. In embodiments where the shaft is used, the markers can be positioned on an inner or outer surface of the shaft or within a thickness of the shaft. Marker 151 may comprise one or more markers oriented parallel to a longitudinal axis of balloon 112, as shown. Mark 151 is typically positioned to be viewed in each 360° rotation of imaging assembly 115, such as to be included in each cross sectional image of lumen L produced by OCT device 100. Mark 151 is typically further positioned to be viewed by camera 200, such that images created by camera 200 can be radially or otherwise registered with images created by OCT device 100. In one embodiment, such as is illustrated in FIG. 1A marker 151 wraps around the proximal end 116 of balloon 112 such as to be viewed by camera 200, while being axially aligned with the major axis of balloon 112. Multiple markers may be placed along a circumference of balloon 112, such as one or more markers positioned approximately 180° from marker 151, such as to register images and/or to determine variations in angular velocity of imaging assembly 115, such as to reduce non-uniform rotational distortion (NURD).

OCT Device 100 may further include registration markers 156 and 157, each positioned on an inner or outer surface of balloon 112, and/or within the wall thickness of balloon 112. Markers 156 and 157 may comprise one or more markers oriented along a partial circumference of balloon 112, as shown. Markers 156 and 157 are typically positioned to be viewed by imaging assembly 115 when imaging assembly 115 is at pre-determined longitudinal positions (e.g. during a translation when OCT device 100 is configured to produce three-dimensional images of lumen L). Images including representations of markers 156 and/or 157 may be correlated to the specific locations of balloon 112 to which they are positioned, such as to provide longitudinal registration information for one or more images produced by OCT device 100. Further longitudinal image registration can be performed by correlating a second image created subsequent to a first image, wherein the first image includes a representation of markers 156 and/or 157, and the longitudinal position of the second image is determined by accounting for translational velocity of imaging assembly 115. For example, if inner member 111 and imaging assembly 115 translate at 0.5 mm/sec, a second image produced 3 seconds from a first image including the distal end of registration marker 156 will comprise an image 1.5 mm from the distal end of registration marker 156.

OCT Device 100 may further include registration marker 158, positioned on an inner or outer surface of shaft 110, and/or within the wall thickness of shaft 110. Marker 158 is positioned to be visible by camera 200. Marker 158 is positioned with known radial and longitudinal offsets to markers 151, 156 and/or 157, such that images produced by camera 200 can be radially, longitudinally or otherwise registered to images produced by OCT device 100 that include representations of markers 151, 156 and/or 157. Alternatively or additionally, marker 158 can be used to longitudinally position balloon 112, such as manually or automatically through the geometric position detection of marker 158 from images provided by camera 200. In a particular embodiment, camera 200 comprises a stereoscopic camera, such as the stereoscopic camera described with reference to FIG. 5 and the depth information provided by the stereoscopic image correlates to marker 158, and thus balloon 112 and its distance from the distal end of camera 200 and/or endoscope 20.

Tissue marker 161, pre-existing in lumen L or created by a device or assembly of system 10 as is described hereabove, may be used to radially, longitudinally or otherwise register one or more images produced by system 10. Camera 200 may create one or more images including representations of tissue marker 161 such as when balloon 112 is deflated or partially inflated. OCT device 100 may produce one or more images including a representation of tissue marker 161, such as when balloon 112 is inflated and imaging assembly 115 is longitudinally aligned with at least a portion of tissue marker 161.

Markers 151, 156, 157, 158 and 161 may be used singly or in combination to provide registration information between one or more images produced by system 10. Alternatively or additionally, markers 151, 156, 157, 158 and 161 may be used singly or in combination to position (e.g. to advance, retract and/or rotate) one or more components of system 10, such as OCT device 100 and/or camera 200. Markers 151, 156, 157 and/or 158 may be positioned at known radial and/or longitudinal offsets, such that when viewed in one or more images, the known offset provides registration and/or other data. Marks 151, 156, 157 and/or 158 may be constructed and arranged to provide registration data of a first image to a second image, registration data of a first image to a component of system 10 and/or registration data of a first image to a portion of a patient's anatomy.

Markers 151, 156, 157 and 158 may comprise material that is configured to absorb, reflect and/or scatter one or more forms of electromagnetic radiation. In one embodiment, one or more markers 151, 156, 157 and 158 are reflective and/or absorptive to visible light, such as visible light used by camera 200. Alternatively or additionally, one or more markers 151, 156, 157 and 158 are reflective and/or absorptive to infrared light, such as infrared light used by OCT device 100. Markers 151, 156, 157 and 158 may be configured to scatter light, such as visible or infrared light. Markers 151, 156, 157 and 158 include one or more components such as, for example a wire (e.g. a 20-30 micron wire), a metal foil, a metal strip, an ink, a dye, and/or combinations of thereof. In some embodiments, system 100 includes an ultrasound imaging device, such as an ultrasound imaging device described with reference to FIG. 5 herebelow. In these embodiments, markers 151, 156, 157 and 158 may absorb, reflect and/or scatter ultrasound. Markers 151, 156, 157 and 158 may include one or more projections, geometric shapes or other identifiable structures that are imagable by system 10 and/or modify the shape of something visible to system 10. In one embodiment, balloon 112 includes one or more tissue deforming projections, such as described with reference to FIG. 4 herebelow, wherein the deformed tissue provides image registration data.

The view image represented in FIG. 1A is a representative drawing of a typical image captured by camera 200 of FIG. 1. Device 100 includes balloon 112, attached to shaft 110 and shown in a partially inflated state. Balloon 112 includes registration marker 152 on proximal end 116, wherein marker 152 is radially aligned with marker 151. In some embodiments, marker 152 and marker 151 comprise a single elongate marker that wraps around from the side of balloon 112 to its proximal end 116. With balloon 112 partially inflated, tissue marker 161 is visible to camera 200. After inflation of balloon 112, tissue marker 161 may be obscured by balloon 112. In these configurations, registration information may be collected by one or more images from camera 200, prior to full inflation of balloon 112.

Figure 2:
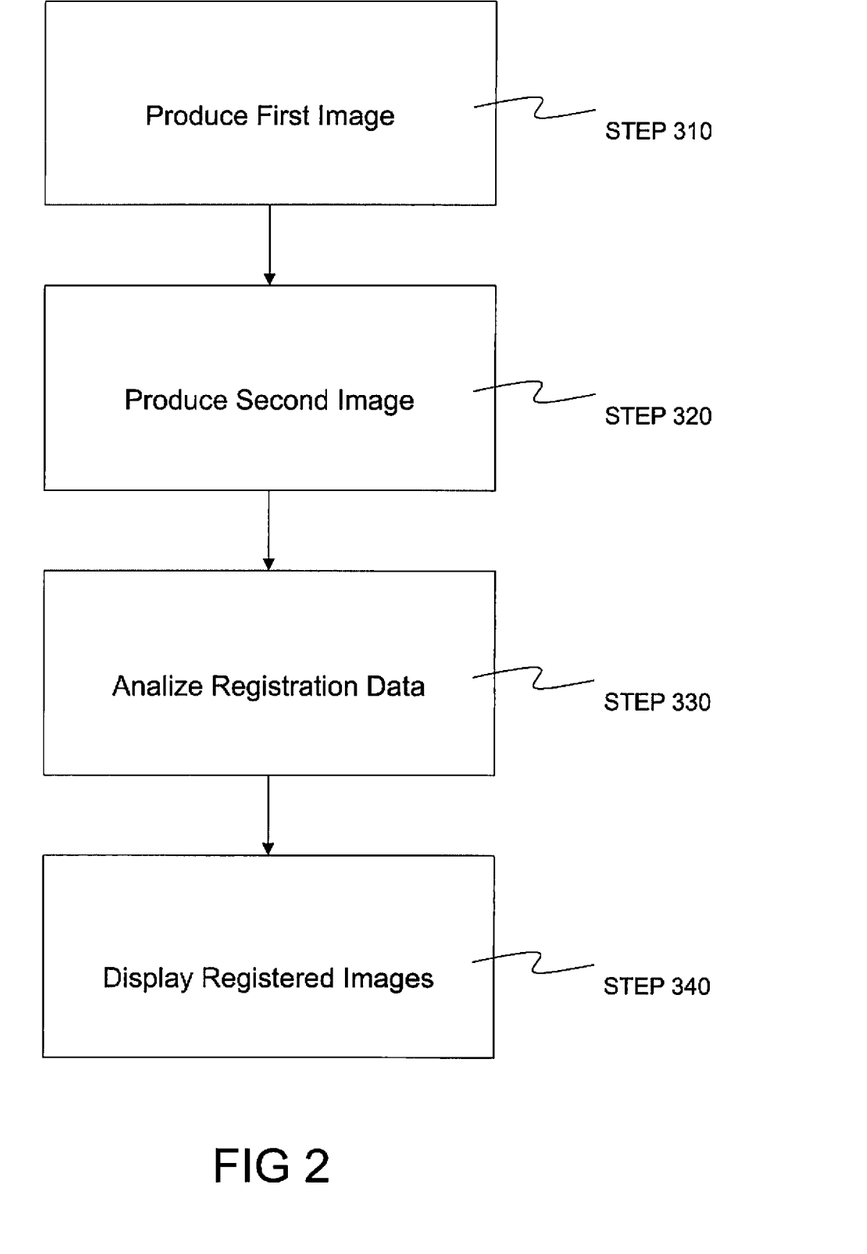
FIG. 2 is a flow chart of a method for producing registration data for multiple images, in accordance with the principles of the present disclosure.

FIG. 2, is a flow chart of a method for producing registration data for multiple images. In step 310, a first image is produced by a first imaging device, such as an image produced by camera 200 of FIG. 1. In step 320, a second image is produced by a second imaging device, such as OCT device 100 of FIG. 1. Alternatively, the first and second images can be produced by a single imaging device, such as two images produced by OCT device 100 of FIG. 1. The first and second images produced in steps 310 and 320 can be produced sequentially or simultaneously. The first and second images each include registration data, such as registration data correlating to representations of one or more registration markers, such as markers 151, 156, 157, 158 and/or 161 of system 10 of FIG. 1.

In step 330, registration data included in the first and second images is analyzed. In step 340, registration information is displayed, for example, on a video monitor (not shown). Registration information may include quantitative or other data representing angular or linear displacements between the first and second images. Registration information may include displaying the first and second images such that they are similarly oriented to the operator, the patient and/or another frame of reference. Registration information may include displaying the first image superimposed on the second image, with proper alignment. The registration information may include displaying a sub-portion of the first image superimposed on a full or partial second image.

A first image may comprise an end view image (see FIG. 1A), such as an image produced by camera 200 of FIG. 1. The second image may comprises multiple cross-sectional images, or slices as described hereabove in reference to a three-dimensional imaging producing OCT device 100 of FIG. 1. The registration information may provide angular or longitudinal registration information between the first image and one or more of the second images, such as registration images between the first image and a three dimensional collection of slice images.

It is contemplated that in the imaging system described herein, an operator can rotate the display of the first image or the second image, in a manual, semi-automatic or fully automated mode. It is also contemplated that in the imaging system described herein, the system can manually or automatically rotate the first image and/or the second image to a known orientation, such as the same orientation as the patient being imaged, such as when the patient is positioned face up on an operating table, and the images are oriented such that anterior locations are positioned above posterior locations on a video monitor.

Alternatively or additionally, registration information may include registration between a first image and a component of the imaging system and/or between a first image and a location in the patient's anatomy.

Figure 3:
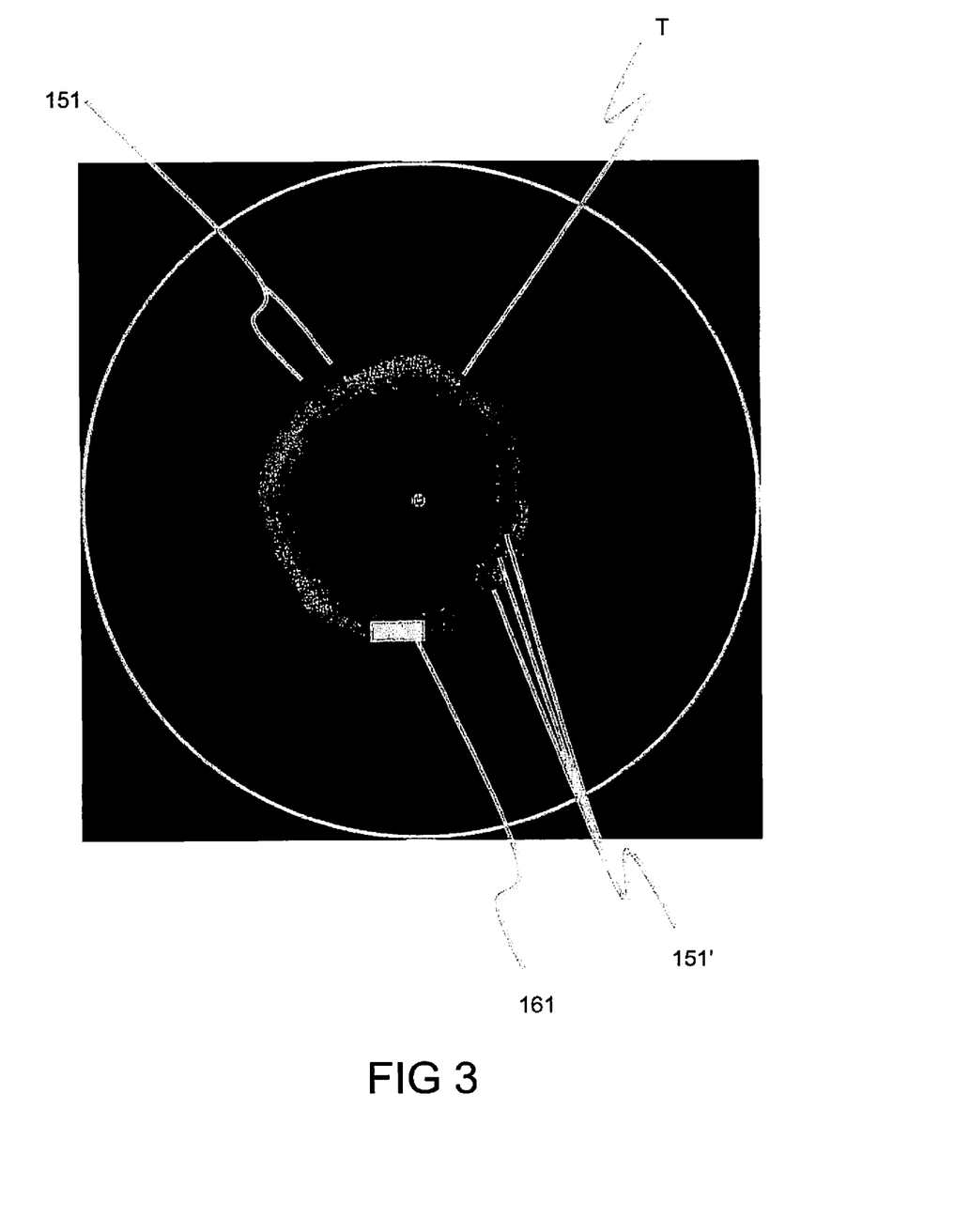
FIG. 3 is an image produced by the imaging system in accordance with the principles of the present disclosure.

The image shown in FIG. 3 may represent an OCT image, such as single slice image provided by OCT device 100 of FIG. 1. The image includes data representing Tissue T, as well as data representing a first marker 151 comprising two linear elements and data representing a second marker 151' comprising three linear elements. Also shown is data representing a tissue marker 161. The image shown in FIG. 3 can be registered to a second image, such as a second OCT image or an image from a visible light camera positioned in an endoscope, for example, the image shown in FIG. 1A. The second image may include a representation of one or more of tissue marker 161, marker 151 or marker 151', such that the one or more representations allow rotational registration of the second image to the first image.

Figure 4:
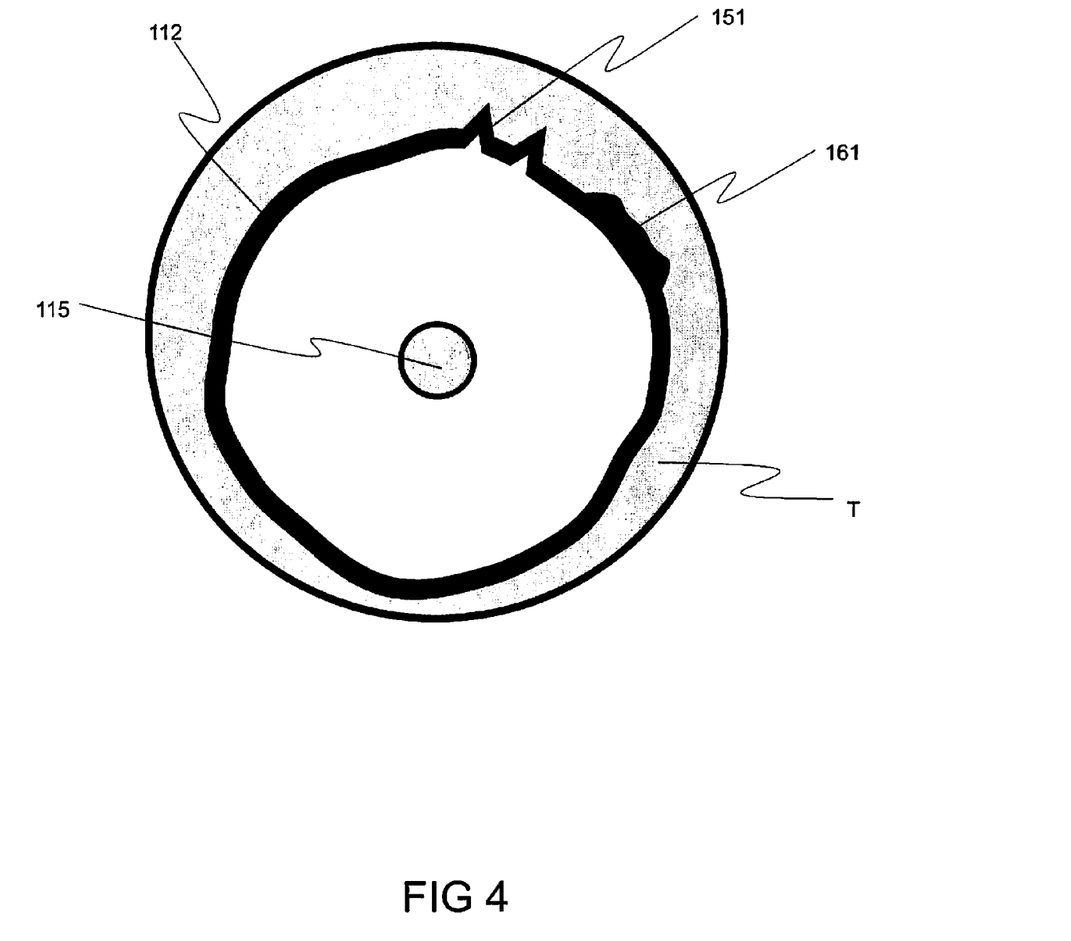
FIG. 4 is a cross sectional view of a distal portion of the imaging system comprising projecting registration markers and a tissue registration marker in accordance with the principles of the present disclosure.

In FIG. 4, an end sectional view of a distal portion of an imaging system comprising projecting registration markers and a tissue registration marker is illustrated. An imaging assembly 115, such as imaging assembly 115 of OCT device 100 of FIG. 1, is positioned approximately in the center of balloon 112. Balloon 112 includes multiple triangle shaped projections 151, which are configured as registration elements of the present invention. Projections 151 are of sufficient rigidity to deform the Tissue T at a location to be imaged by the OCT device as well as one or more other image producing devices such as camera 200 of FIG. 1. Projections 151 may continue on the proximal end of balloon 112, and/or they may be aligned with one or more separate markers, such as markers 152. The tissue deformations can be used to radially register one or more images produced by the one or more imaging devices. A tissue marker 161 may also be included for radial and/or longitudinal registration.

Figure 5:
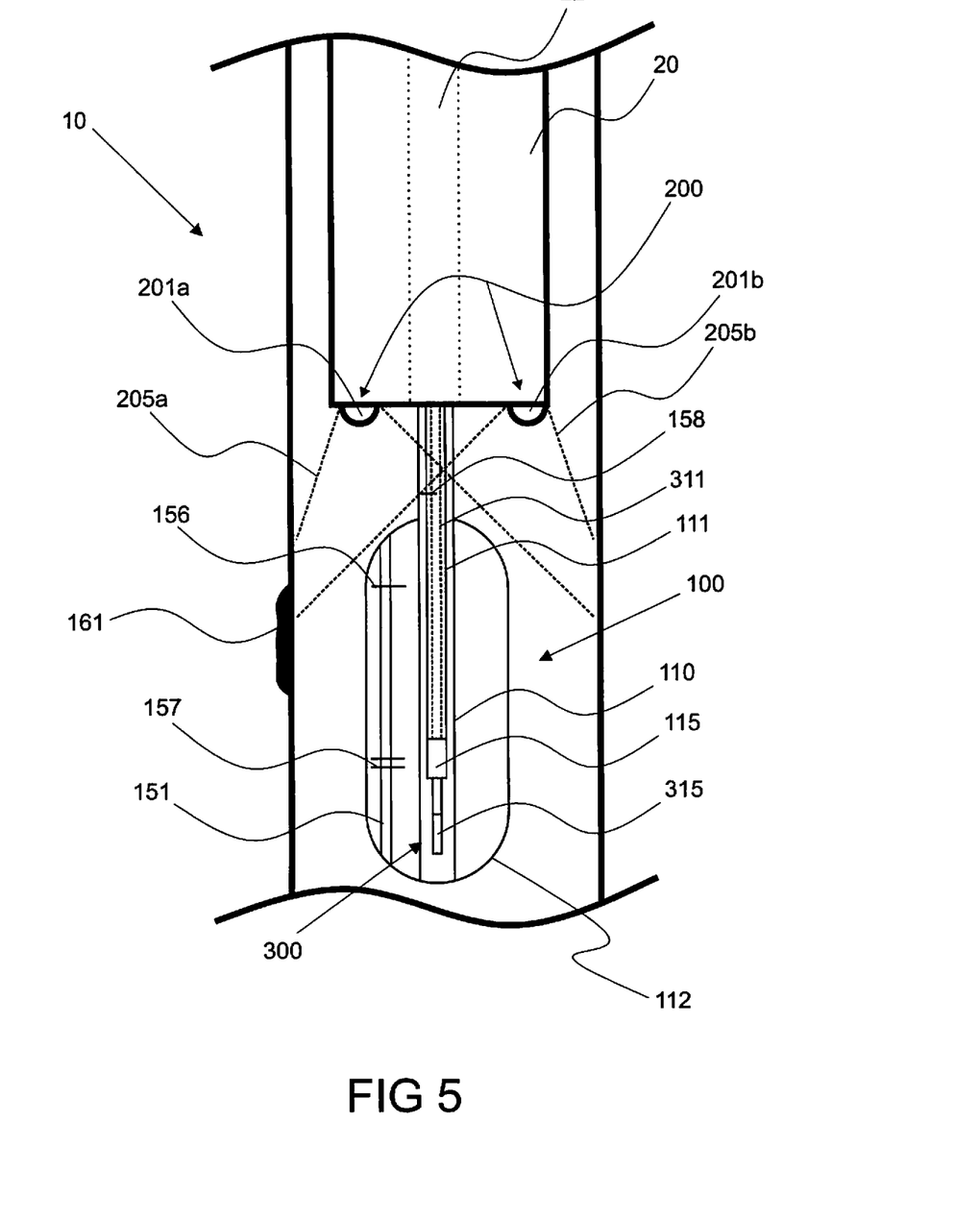
FIG. 5 is a side view of a distal portion of an imaging system comprising registration marks and three imaging devices in accordance with the principles of the present disclosure.

In FIG. 5, a side view of a distal portion of an imaging system comprising registration marks and three imaging devices is illustrated. System 10 includes an endoscope 20, a first imaging device 200, e.g. a stereoscopic camera, a second imaging device 100, e.g. a OCT device, and a third imaging device 300, e.g. an ultrasound imager. Stereoscopic camera 200 including lenses 201a and 201b, includes fields of view 205a and 205b, respectively. OCT device 100 is constructed and arranged to produce an OCT image. OCT device 100 includes an elongate shaft 110, which has been slidingly passed through working channel 22 of endoscope 20. OCT device 100 includes balloon 112 of similar construction to balloon 112 of FIG. 1. Other configurations can replace balloon 112 with a shaft as described above. OCT device 100 includes inner member 111 with distally mounted imaging assembly 115. Imaging assembly 115 is configured similar to imaging assembly 115 of FIG. 1, such as to produce a two-dimensional image of the plane orthogonal to a rotating imaging assembly 115. Imaging assembly 115 may be configured to both rotate and translate such as to produce a three-dimensional image comprising a series of slice images.

Ultrasound imager 300 includes shaft 311 and ultrasound crystal 315. Inner member 111 of OCT device 100 includes an inner shaft through which shaft 311 is slidingly received. In an alternative embodiment, inner member 111 and shaft 311 are positioned in a side by side configuration. In another alternative embodiment, inner member 111 comprises shaft 311, such that imaging assembly 115 and ultrasound crystal 315 are mounted to a single shaft, such as a shaft comprising a fiber optic cable and one or more electrical wires.

At the distal end of shaft 113 is ultrasound crystal 315, configured to transmit and receive ultrasound waves, such as to produce a two-dimensional image of the plane orthogonal to crystal 315. Similar to the image creation of imaging assembly 115, crystal 315 is constructed and arranged to produce a two-dimensional image of the plane orthogonal to a rotating crystal 315. Crystal 315 may be configured to both rotate and translate, such as to produce a three dimensional image comprising a series of slice images. Rotation of shaft 311 may be in the same direction as the rotation of inner member 111 or in the opposite direction, such as to prevent undesired twisting.

System 10 of FIG. 5 includes one or more markers 151, 156, 157, 158 and 161, typically of similar construction and placement as the markers with the same reference numbers described hereabove with reference to FIG. 1. In addition, markers 151, 156, 157 and/or 161 may be configured to be distinguishable in an ultrasound image produced by ultrasound imager 300, such as when markers 151, 156, 157 and/or 161 are configured to absorb, reflect and/or scatter ultrasonic waves.

Figure 6:
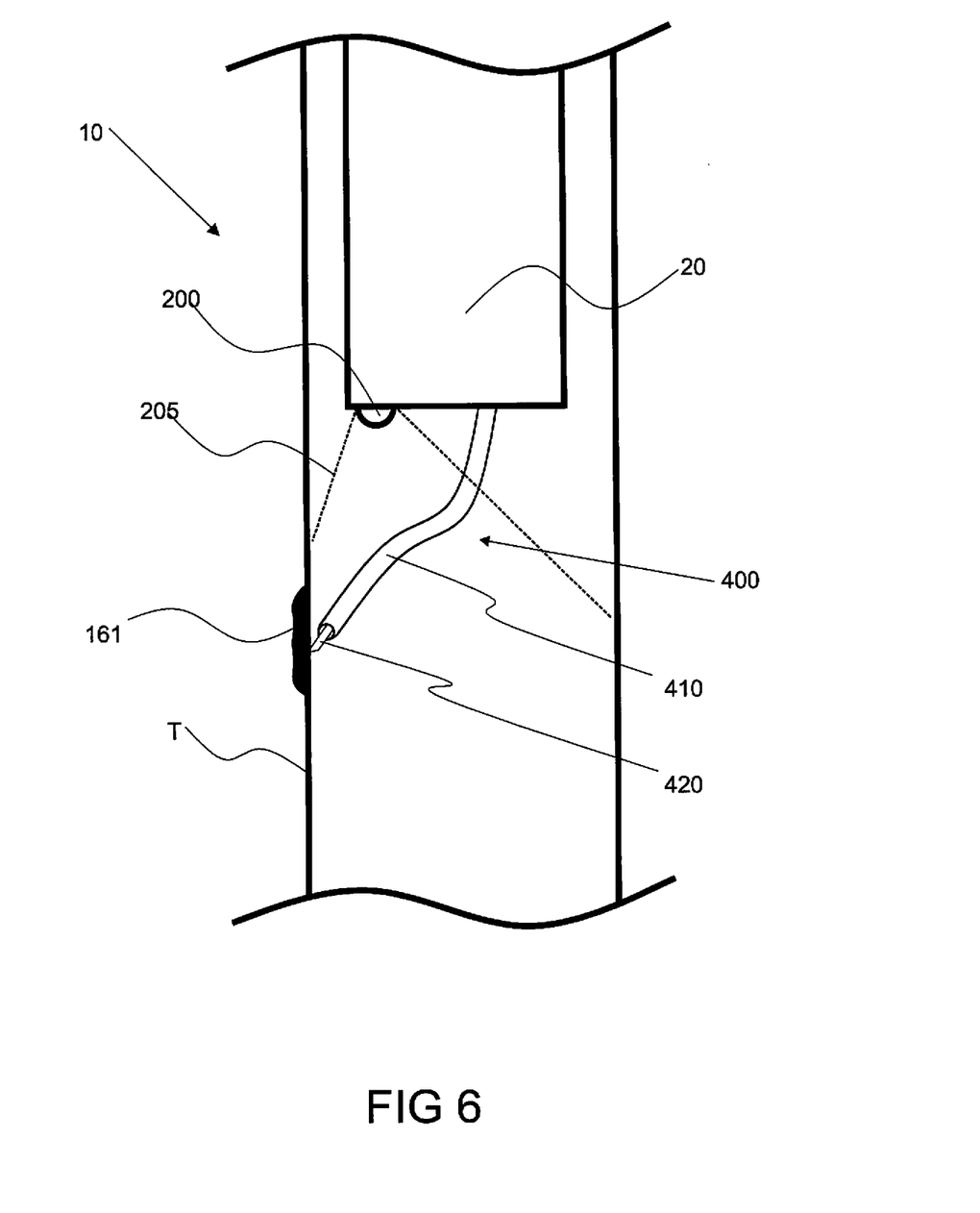
FIG. 6 is a side view of a distal portion of a system including an advanceable, elongate tissue marking device in accordance with the principles of the present disclosure.

In FIG. 6, a side view of a distal portion of a system including an advanceable, elongate tissue marking device is illustrated. System 10 includes endoscope 20 and camera 200. System 10 further includes tissue marking device 400, shown having been advanced through a working channel of endoscope 20, such as a working channel also configured to receive to a second imaging device such as OCT device 100 of FIG. 1.

Tissue marking device 400 includes a shaft 410 and an advanceable prove 420. It is contemplated that probe 420 may include a needle such as a needle configured to deliver dye, ink or other tissue marking substance, an energy delivery element such as an electrode configured to deliver radiofrequency energy or a fluid conduit configured to deliver cryogenic fluid, a cannula configured to deliver an implant such as a temporary implantable filament, a biopsy or other tissue removal element, and various combinations thereof. Probe 420 is shown in FIG. 6 in contact with Tissue T such as to create tissue marker 161. Camera 200 comprises field of view 205 configured to view the tissue marking process completed with device 400.

Figure 7A:
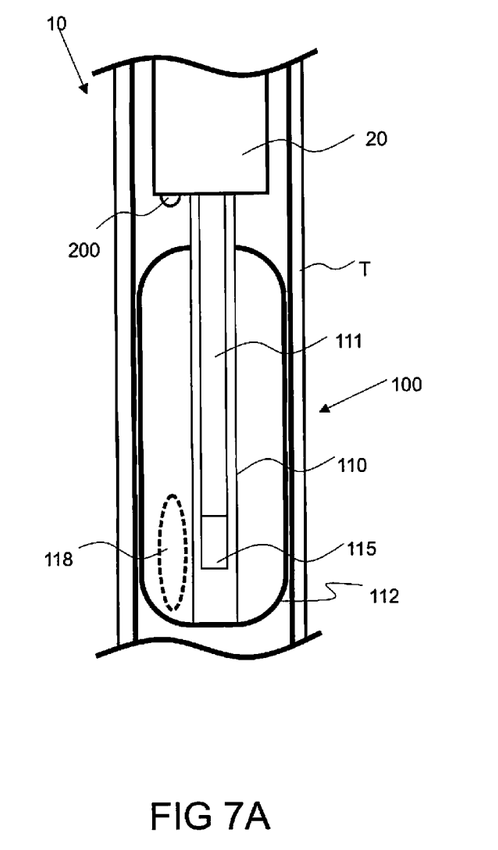
FIGS. 7A and 7B are side views of a distal portion of a system including a balloon configured to mark tissue, prior to and after tissue marking respectively in accordance with the principles of the present disclosure.
Figure 7B:
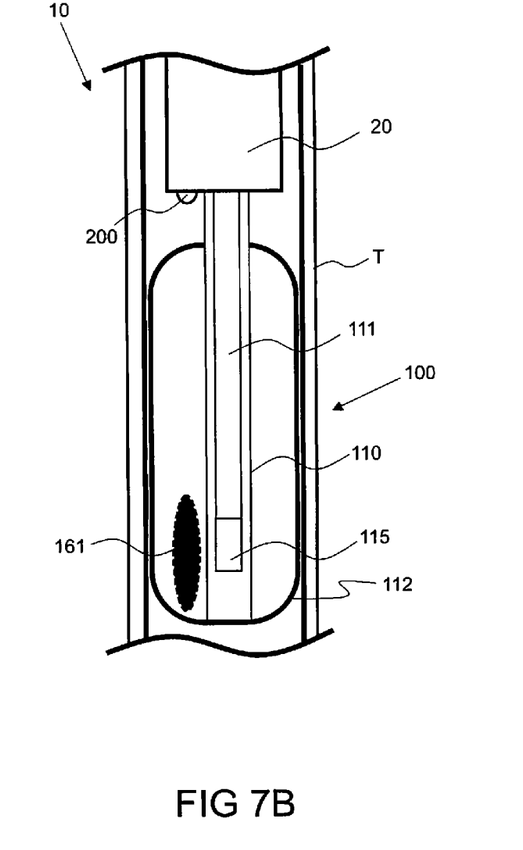

In FIGS. 7A and 7B, side views of a distal portion of a system including a balloon configured to mark tissue, prior to and after tissue marking respectively, are illustrated. System 10 includes endoscope 20 and camera 200. System 10 further includes OCT device 100, which has been configured to both produce an OCT image as described hereabove in reference to FIG. 1, as well as to produce a registration mark of the present invention, tissue marker 161.

OCT device 100 includes outer shaft 110, inner rotating inner member 111 and imaging assembly 115, each of similar construction and arrangement as the similar components of FIG. 1. Balloon 112 includes a deployable marker 118, positioned on the outer surface of balloon 112, and configured to be operably deployed to create tissue marker 161. It is contemplated that deployable marker 118 can include an ink or dye such as an ink or dye configured to be released from balloon 112 with the application of energy such as laser energy emitted from imaging assembly 115, a foil or other transfer material configured to be transferred to the tissue such as with the application of pressure and/or heat, an implant such as a filament configured to penetrate at least a portion of Tissue T and various combinations of thereof.

In FIG. 7A, deployable marker 118 is shown in its pre-deployed state. In FIG. 7B, marker 118 has been deployed creating tissue marker 161. Marker 118 may comprise one or more materials configured to be identified in one or more images produced by an imaging device of system 10. In typical embodiments, marker 118 can include a material configured to absorb, reflect and/or scatter one or more of visible light, infrared light, ultrasonic waves; other forms of electromagnetic radiation, and various combinations thereof.

Figure 8:
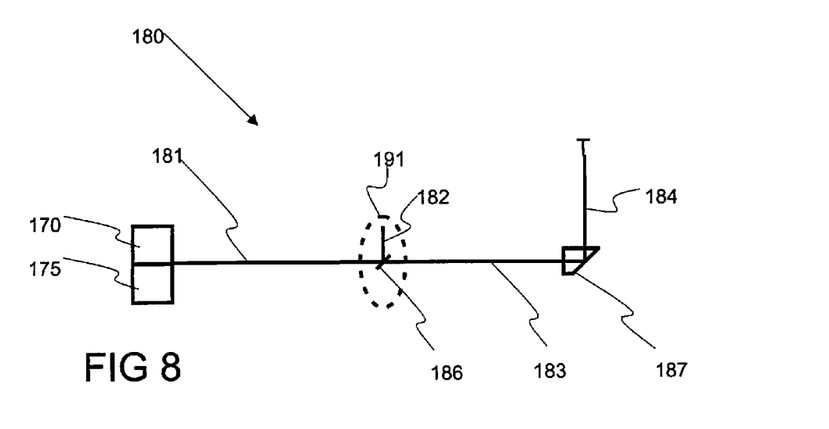
FIG. 8 is a schematic diagram of an optical subsystem including a registration pattern circumferentially surrounding an optical fiber in accordance with the principles of the present disclosure.

In FIG. 8, a schematic diagram of an optical subsystem including a registration pattern circumferentially surrounding an optical pathway is illustrated. Optical subsystem 180, includes a first optical pathway 181, typically comprising one or more optical fibers. Pathway 181 receives light from a proximal source 170, such as a laser source commonly used in OCT imaging devices. A beam splitter 186 is positioned at the distal end of pathway 181, and divides the transmitted light into orthogonal pathway 182 and continuing (i.e. in-line) pathway 183. In a typical embodiment, a small percentage of the light received by beam splitter 186 is directed toward orthogonal pathway 182. For example, beam splitter 186 might be configured to split the light in percentages such as 99/1, 95/5 or 90/10 with the greater percentage being directed to the tissue imaging and the lesser percentage being directed to detecting the registration pattern. Distal to beam splitter 186 is prismatic mirror 187, which deflects the transmitted light from pathway 183 to create a second orthogonal pathway 184. First orthogonal pathway 182 is directed toward a circumferential registration pattern 191, to produce a registration pattern for example, registration pattern 191a, 191b or 191c of FIGS. 8A, 8B and 8C, respectively. Second orthogonal pathway 184 is directed toward the lumen of tissue to be imaged, such as in the OCT image devices described hereabove.

Registration pattern 191 can be placed on the inside of a shaft which surrounds pathway 181, such as a pattern adhesively attached to, or marked upon, the inner wall of the shaft, or positioned on the inside or outside of the balloon 112 (or shaft in alternate configurations). Other positions and placement methods are contemplated.

Beam splitter 186 and prismatic mirror 187 are configured to be synchronously rotated, such that pathway 182 rotates along circumferential marker 191 and pathway 184 rotates circumferentially about tissue, such as in the configuration described in reference to inner member 111 and imaging assembly 115 of FIG. 1 hereabove. Beam splitter 186 and prismatic mirror 187 may be further configured to translate, such as to create a three-dimensional OCT image. In these configurations, registration pattern 191 has a length sufficient to be continuously viewed during full translational displacement.

Reflected light from Tissue T travels proximally via pathway 184 to prismatic mirror 187. Prismatic mirror 187 deflects the reflected light toward beam splitter 186 via pathway 183. Reflected light from circumferential registration pattern 191 travels proximally via pathway 182 to beam splitter 186. The reflected light from tissue T and circumferential registration pattern 191 are combined in beam splitter 185 and travels proximally to sensor 175 via pathway 181. Sensor 175 may comprise an interferometric sensor assembly commonly used in OCT imaging devices, configured to convert coherent reflected light signals into images.

Path length differences in the reflections received from the tissue T and the circumferential registration pattern 191 will produce interferometric signals with different frequencies and may be used to decode the received signal into correlated registration pattern and tissue image information.

Numerous configurations of registration patterns may be employed as the circumferential registration pattern 191. Various configurations of series of monochromatic or varying chroma shapes, such as lines, can be used to indicate rotational orientation or displacement of optical pathway 184 and/or prismatic mirror 187, due to the fixed alignment with beam splitter 186 and pathway 182. These configurations can be employed to indicate absolute as well as differential rotational orientation, such as those used in optical encoder registration patterns known to those of skill in the art. In the configuration shown in FIG. 8A, circumferential registration pattern 191a comprises multiple sets of repeated patterns of increasing width lines, such as to indicate a differential rotational orientation. In the configuration shown in FIG. 8B, circumferential registration pattern 191b comprises a single series of increasing width lines such as to indicate an absolute rotational orientation.

Figure 8A:
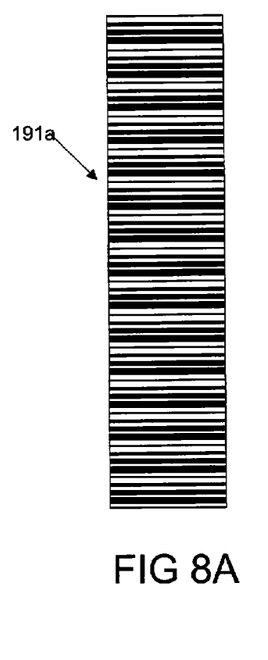
FIGS. 8A, 8B and 8C are differing patterns of registration marks in accordance with the principles of the present disclosure.
Figure 8B:
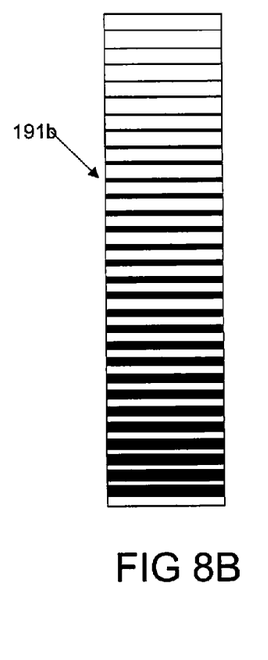
Figure 8C:
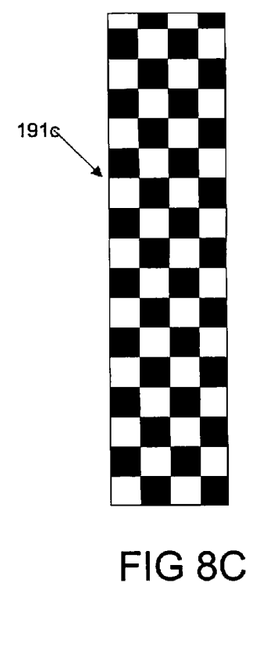

The registration patterns of FIGS. 8A and 8B provide radial registration information, such as when prismatic mirror 187 is receiving reflections of light from tissue T while rotating, similar to the information received from registration mark 151 of FIG. 1. Circumferential registration pattern 191c shown in FIG. 8C, provides both radial and longitudinal information, such as the information provided by the combination of markers 151 and 156 and/or 157 described hereabove.

Figure 9A:
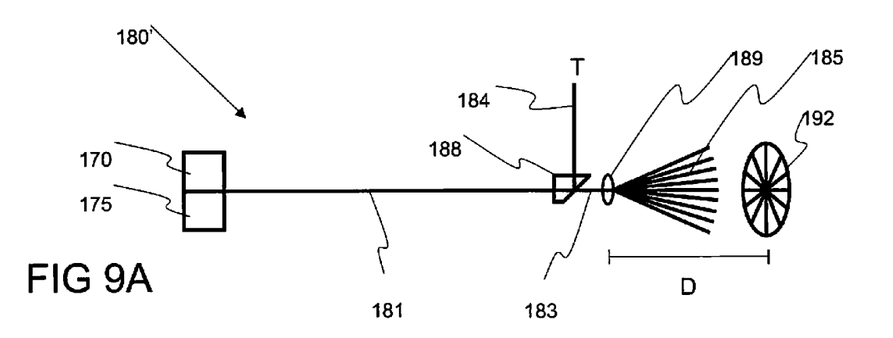
FIG. 9A is a schematic diagram of an optical subsystem including a registration pattern placed distal to and in-line with an optical fiber in accordance with the principles of the present disclosure.

In FIG. 9A, a schematic diagram of an optical subsystem including a registration pattern placed distal to and in-line with an optical pathway is illustrated. Optical subsystem 180' includes a first optical pathway 181, typically comprising one or more optical fibers. Pathway 181 receives light from a proximal source 170, such as a laser source commonly used with OCT imaging devices. A prismatic beam-splitting mirror 188 is positioned at the distal end of pathway 181 and divides the transmitted light into orthogonal pathway 184 and continuing (i.e. in-line) pathway 183. In a typical embodiment, a small percentage of the light received by prismatic beam-splitting mirror 188 is directed toward continuing pathway 183. For example, beam splitter 186 might be configured to split the light in percentages such as 99/1, 95/5 or 90/10 with the greater percentage being directed to the tissue imaging and the lesser percentage being directed to detecting the registration pattern. Distal to prismatic beam-splitting mirror 188 is circular lens 189, which directs the light from pathway 183 into spread-focus pathway 185. Orthogonal pathway 184 is directed toward the lumen of the tissue to be imaged, such as in OCT imaging devices described hereabove. Spread-focus pathway 185 is direct toward a distal registration pattern 192, such as registration pattern 192 shown in FIGS. 9C and 9D. Spread-focus pathway 185 comprises a full diameter line at the surface of registration pattern 192.

Registration pattern 192 is typically positioned at a distal portion of a shaft, facing proximally, and in-line with spread-focus pathway 185. Pattern 192 is typically adhesively attached to or otherwise marked upon an inside surface of the shaft.

Figure 9B:
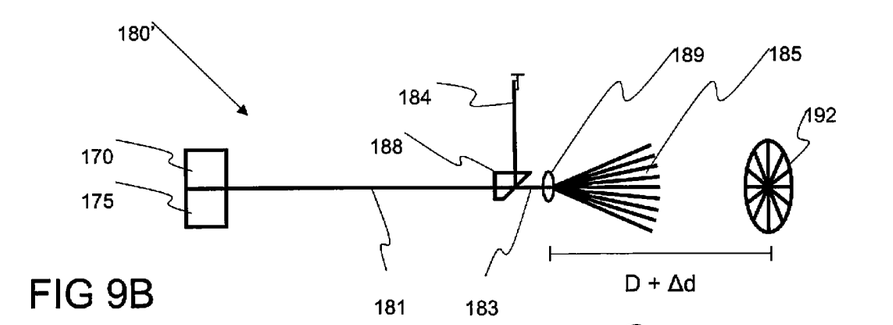
FIG. 9B is a schematic diagram of the optical subsystem of FIG. 9A with the optical fiber moved proximally, away from the registration pattern in accordance with the principles of the present disclosure.

Prismatic beam-splitting mirror 188 and circular lens 189 are configured to be synchronously rotated such that pathway 184 rotates circumferentially about tissue, such as in the configuration described in reference to inner member 111 and imaging assembly 115 of FIG. 1. Prismatic beam-splitting mirror 188 and circular lens 189 may be further configured to translate, such as to create a three-dimensional OCT image. In these configurations, the length D of spread focus pathway 185 varies with the linear translation of prismatic beam-splitting mirror 188 and circular lens 189, such as with a change in distance of Δd as shown in FIG. 9B. Light reflected and detected from the registration pattern can be encoded using an interferometric frequency based on the path length difference to a predefined nominal zero delay location. As the probe moves further away from the registration pattern, light reflected from the pattern will possess a higher frequency, thus enabling the decoding of the longitudinal distance.

Reflected light from tissue T travels proximally via pathway 184 to prismatic beam-splitting mirror 188. Reflected light from registration pattern 192 travels proximally via pathway 185 to circular lens 189. Circular lens 189 focuses the received reflection towards prismatic beam-splitting mirror 188 via pathway 183. The reflected light from tissue T and registration pattern 192 are combined in prismatic beam-splitting mirror 188 and travels proximally to sensor 175 via pathway 181. Sensor 175 may comprise a sensor assembly commonly used in OCT imaging devices, configured to convert reflected light signals into images.

Path length differences in the reflections received from the tissue T and the circumferential registration pattern 191 may be used to decode the received interferometric signal into correlated registration pattern and tissue image information.

Numerous configurations of patterns for registration pattern 192 may be employed. Patterns may be configured to provide differential and/or absolute rotational position information, as is described in reference to FIGS. 8C and 8D hereabove.

Figure 9C:
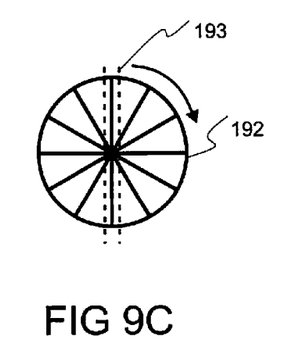
FIG. 9C is a registration pattern of FIGS. 9A and 9B in a first rotational orientation of the optical fiber in accordance with the principles of the present disclosure.
Figure 9D:
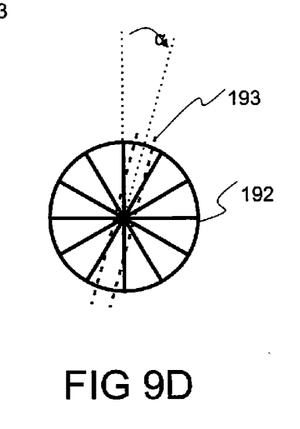
FIG. 9D is a registration pattern of FIGS. 9A and 9B in a second rotational orientation of the optical fiber.

Referring now to FIGS. 9C and 9D, optical pathway 185 is oriented to create linear viewing window 193 on registration pattern 192. In FIG. 9C, window 193 is oriented vertically as shown. As prismatic beam-splitting mirror 188 and circular lens 189 rotate, window 193 rotates with respect to registration pattern 192, such as to the position shown in FIG. 9D, a degrees clockwise from vertical. The reflected image of registration pattern as seen via viewing window 193 is used to encode rotational orientation or displacement.

In addition to rotational position information, optical subsystem 180' is configured to provide information about the longitudinal position of prismatic beam-splitting mirror 188, such as the information provided by the combination of markers 151 and 156 and/or 157 of FIG. 1.

Figure 10:
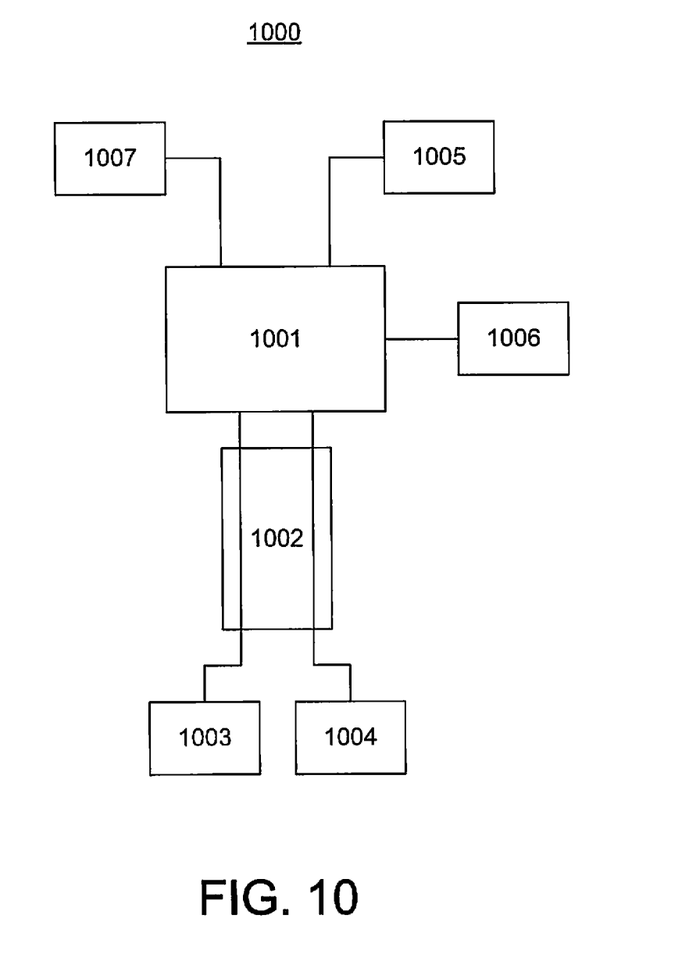
FIG. 10 is a block diagram of a system for registering images n accordance with the principles of the present disclosure.

FIG. 10 is a block diagram of an overall system for producing and registering images in accordance with the present disclosure. The system for producing and registering images 1000 includes a processor 1001 configured to receive signals from imaging devices 1003 and 1004, as discussed above, although the system 1000 is described with respect to FIG. 10 as using more than one imaging device to produce more than one image, the principles of the present disclosure are applicable to a system having only one imaging device for producing more than one image. Imaging devices 1003, 1004 are illustrated as extending through cannula 1002. As described above, cannula 1002 can be an endoscope with one of imaging devices 1003, 1004 attached thereto. Also included in system 1000 is memory 1005 in communication with processor 1001. Memory 1005 can include programs for controlling system 1001 as well as for storing image data produces by imaging devices 1003, 1004. System 1000 also include a display for displaying images produces by the imaging devices 1003, 1004. The images can be displayed independently of in an overlaid fashion. Processor 1001 can orient and scale the displayed images to properly register the images with each other. In addition, although illustrated as one display, more than one display is contemplated. System 1000 also can include input/output (I/O) devices 1007 such as a keyboard, touch screen, mouse, to provide additional control over the components of the system. For example, I/O device 1007 can include a dial configured to allow a user to rotate an image by rotating the dial for manual registration of the images. As another example, a slide potentiometer can be an I/O device configured to allow a user to scale an image by sliding the potentiometer for manual registration of the images.

While the preferred embodiments of the devices and methods have been described in reference to the environment in which they were developed, they are merely illustrative of the principles of the inventions. Modification or combinations of the above-described assemblies, other embodiments, configurations, and methods for carrying out the invention, and variations of aspects of the invention that are obvious to those of skill in the art are intended to be within the scope of the claims.

In addition, where this application has listed the steps of a method or procedure in a specific order, it may be possible, or even expedient in certain circumstances, to change the order in which some steps are performed, and it is intended that the particular steps of the method or procedure claim set forth herebelow not be construed as being order-specific unless such order specificity is expressly stated in the claim.

What is claimed is:

1. A system configured for producing registered images of a body cavity, comprising:

a first imaging device having an imager positioned at a distal end thereof, said first imaging device configured to produce a first image of a body cavity; and an imaging system, comprising:
a second imaging device having an imager positioned at a distal end thereof and configured to be positioned approximate to said imager of said first imaging device within said body cavity and configured to produce a second image of the body cavity,
an elongated member extending along a longitudinal axis between opposite proximal and distal ends, the elongated member comprising an inner surface defining a passageway having said second imaging device rotatably disposed therein,
a balloon coupled to the elongated member, the balloon comprising a first marker configured to produce registration information in the first image and the second image, the first marker extending parallel to the longitudinal axis, and
a processor configured to register the first and second images based on the registration information in the first and second images, and
wherein the first imaging device is a camera and the second imaging device is an optical coherence tomography (OCT) imaging device translatable and rotatable with respect to the first imaging device.

2. The system of claim 1, wherein said first marker is configured to convey at least one of translation and rotation information of the OCT imaging device within the registration information in the second image and said first marker comprises material that is configured to absorb, reflect and/or scatter one or more forms of electromagnetic radiation.

3. The system of claim 1, further comprising:
an optical device positioned along an optical path of a light source for said OCT imaging device for directing a portion of light from the light source toward said first marker and receive reflected light from said first marker.

4. The system of claim 3, wherein said first marker is an encoder pattern positioned to remain in a fixed location with respect to translation and rotation of the OCT imaging device.

5. The system of claim 4, wherein the portion of light is directed transverse to a light path and toward the encoder pattern positioned circumferentially about said light path to convey translation and rotation information of the OCT imaging device in the registration information in the second image.

6. The system of claim 4, wherein the portion of light is directed substantially along a light path and toward a second marker positioned a distance from a distal end of the OCT imaging device to convey translation and rotation information of the OCT imaging device in the registration information in the second image.

7. The system of claim 1, wherein said registration information in the first and second images conveys a distance between said first and second imaging devices.

8. The system of claim 1, wherein said registration information in the first and second images conveys a rotational offset between said first and second imaging devices.

9. The system of claim 1, wherein:
the camera is a stereoscopic camera;
the system further comprises a third imaging device having an imaging end and configured to produce a third image containing registration information produced by the first marker, the third imaging device being coaxial with the second imaging device; and
the processor registers the first and second images based on the registration information in the first, second and third images.

10. The system of claim 9, wherein said third imaging device is an ultrasound imaging device.

11. The system of claim 1, wherein the processor is configured to register the first and second images by identifying the registration information in the first and second images, scaling the second image based on a size of the registration information in the first and second images and rotating the second image based on an orientation of the registration information in the first and second images.

12. The system of claim 11, wherein said first marker is positioned such that the registration information in the first and second images will be produced in the first and second images, respectively, independent of translation and rotation of the second imaging device relative to the first imaging device.

13. The system of claim 1, wherein the balloon comprises a second marker configured to produce second registration information in the first image and the second image, the second marker extending parallel to the longitudinal axis such that the second marker is positioned 180 degrees from the first marker.

14. The system of claim 13, wherein the first and second markers are embedded within a wall thickness of the balloon.

15. The system of claim 1, wherein the balloon comprises at least one second marker extending parallel to the longitudinal axis and positioned approximately 180 degrees from the first marker.

16. The system of claim 15, wherein the first marker wraps around a proximal end of the balloon so as to be viewed by the camera while being axially aligned with a major axis of the balloon.

17. The system of claim 1, wherein the balloon comprises a plurality of second markers each extending parallel to the longitudinal axis and positioned approximately 180 degrees from the first marker.

18. The system of claim 1, wherein the balloon comprises a second marker that extends transverse to the longitudinal axis, the second marker being spaced apart from the first marker.

19. The system of claim 1, wherein the balloon extends from a proximal end to an opposite distal end, the proximal end of the balloon comprising a second marker, the distal end of the balloon comprising a third marker, the second and third markers each extending transverse to the longitudinal axis such that the second and third markers are spaced apart from one another and from the first marker, the second and third markers being configured to provide longitudinal registration information for the second image.

20. The system of claim 1, wherein:
the camera is a stereoscopic camera and the first image is a stereoscopic image; and the elongated member comprises a registration marker that extends transverse to the longitudinal axis and is visible by the camera, the registration marker being visible in the stereoscopic image to provide depth information correlating to the balloon and a distance of the balloon from a distal end of the camera.

21. A system for registering images, comprising:
a first imaging device and a second imaging device, the first and second imaging devices being configured for producing at least two images within a cavity of a patient, said first imaging device having a distal imaging end;
an elongated member extending along a longitudinal axis between opposite proximal and distal ends, the elongated member comprising an intermediate portion between the proximal and distal ends and an inner surface defining a passageway having the second imaging device rotatably disposed therein;

a balloon having a proximal end coupled to the intermediate portion and an opposite distal end coupled to the distal end of the elongated member, the balloon comprising a first marker positioned relative to the imaging end and configured to produce registration data in each of the images produced by the first and second imaging devices, said first marker extending parallel to the longitudinal axis and positioned such that the registration data in each of the images will be produced independent of translation and rotation of the second imaging device relative to the first imaging device; and a processor in communication with the first and second imaging devices configured to receive said images and register the images based on the registration data in each of the first and second images, wherein the first imaging device is a camera and the second imaging device is an optical coherence tomography (OCT) imaging device translatable and rotatable with respect to the first imaging device.

22. The system of claim 21, wherein the first marker wraps around the proximal end of the balloon so as to be viewed by the camera.

23. The system of claim 21, wherein the processor is further configured to automatically register the images by identifying the registration data in the images and at least one of scaling the second image based on a size of the registration data in the images and rotating the second image based on an orientation of the registration data in the images.

24. A method for registering images in a system having a first imaging device configured to produce a first image and an imaging system including a second imaging device positioned within an elongated member extending along a longitudinal axis between opposite proximal and distal ends, the elongated member comprising an inner surface defining a passageway, said second imaging device being rotatably disposed in the passageway and configured to produce a second image, the imaging system comprising a balloon coupled to the elongated member, comprising the steps of:

inserting said first imaging device into a cavity of a patient;

inserting said elongated member into the cavity of the patient such that the balloon is positioned within the cavity of the patient, said balloon having a first marker visible to both the first and second imaging devices, the first marker extending parallel to the longitudinal axis;

producing by said first imaging device a first image containing an image of said first marker;

producing by said second imaging device a second image containing an image of said first marker; and registering said first image and said second image based on the image of the first marker in the first and second images, wherein the first imaging device is a camera and the second imaging device is an optical coherence tomography (OCT) imaging device translatable and rotatable with respect to the first imaging device.

25. The method of claim 24, wherein said registering step includes:

rotating said second image to orient said image of said first marker in said second image in a same direction as said image of said first marker in said first image; and scaling said second image to size said image of said first marker in said second image to match a size of said image of said first marker in said first image.

26. A system for producing registered images of a body cavity, comprising:

a first imaging device configured to produce a first image of tubular tissue within the body cavity, said first image including first registration data;

a second imaging device constructed and arranged to produce a second image of the tubular tissue within the body cavity, said second image including second registration data;

an elongated member extending along a longitudinal axis between opposite proximal and distal ends, the elongated member comprising an inner surface defining a passageway having the second imaging device rotatably disposed therein; and a balloon coupled to the elongated member and comprising first and second markers configured to produce the first and second registration data, the first and second markers each extending parallel to the longitudinal axis, the second marker being positioned approximately 180 degrees from the first marker, and a processor configured to register the first image to the second image based on the first registration data and the second registration data, wherein the first imaging device is a camera and the second imaging device is an optical coherence tomography (OCT) imaging device translatable and rotatable with respect to the first imaging device.

* * * * *